United States Patent [19]
Paul et al.

[11] Patent Number: 5,145,974
[45] Date of Patent: Sep. 8, 1992

[54] PREPARATION OF NITRATOALKYL-SUBSTITUTED CYCLIC ESTERS

[75] Inventors: Norman C. Paul, Hertfordshire; Ross W. Millar, Essex; Peter Golding, Hertfordshire, all of United Kingdom

[73] Assignee: The Secretary of State for Defence in Her Britannic Majesty's Government of the United Kingdom of Great Britain and Northern Ireland, London, United Kingdom

[21] Appl. No.: 669,405
[22] PCT Filed: Jul. 14, 1989
[86] PCT No.: PCT/GB89/00812
§ 371 Date: Mar. 22, 1991
§ 102(e) Date: Mar. 22, 1991
[87] PCT Pub. No.: WO90/01028
PCT Pub. Date: Feb. 8, 1990

[30] Foreign Application Priority Data
Jul. 22, 1988 [GB] United Kingdom ............... 8817545
Apr. 7, 1989 [GB] United Kingdom ............... 8907852

[51] Int. Cl.$^5$ ............... C07D 301/00; C07D 305/06; C07D 305/04
[52] U.S. Cl. .................... 549/510; 549/511; 549/513
[58] Field of Search .................. 549/513, 510, 511; 558/480

[56] References Cited

U.S. PATENT DOCUMENTS
3,058,994 10/1962 Schrage .................... 549/510
3,549,687 12/1970 Bachman et al. ............ 558/480

OTHER PUBLICATIONS
Eremenko et al. Chem. Absts. vol. 68, No. 9, Feb. 26, 1969, 39373c.

Primary Examiner—J. E. Evans
Attorney, Agent, or Firm—Nixon & Vanderhye

[57] ABSTRACT

A continuous process for producing nitratoalkyl-substituted cyclic ethers which consists of (a) cocurrently mixing a stream of $N_2O_5$ and a stream of a hydroxyalkyl-substituted cyclic ether each dissolved in an inert organic solvent, followed by (b) rapidly separating the nitric acid and nitratoalkyl coproducts before they can react together to rupture the ether ring. Step (b) is conveniently performed by quenching the product stream within approximately 15 seconds of its formation, in a basic aqueous solution into which the nitric acid is transferred from the organic phase and is neutralized. Examples of products which may be prepared by this process are nitratoalkyl-substituted oxiranes and oxetanes.

14 Claims, 1 Drawing Sheet

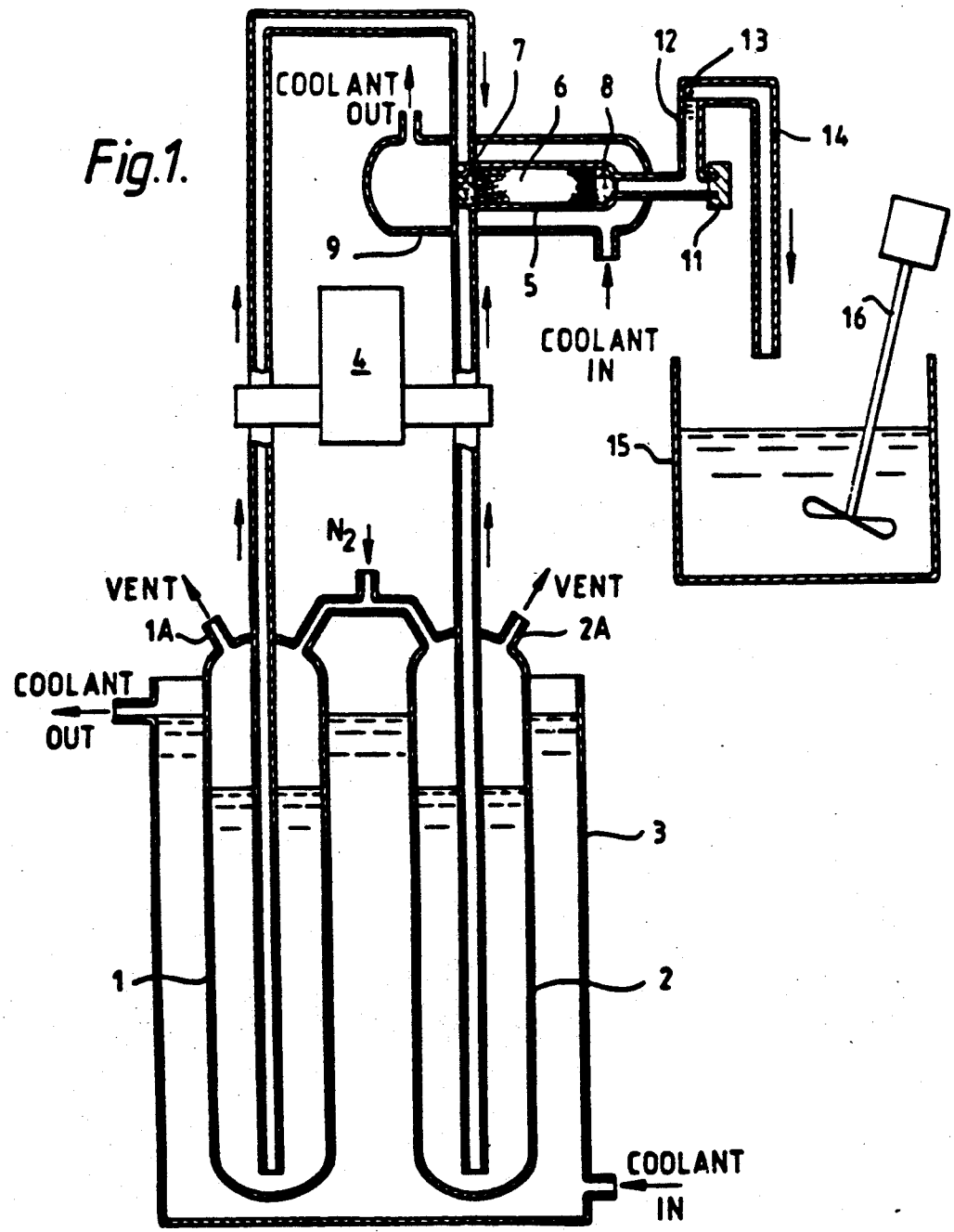

PREPARATION OF NITRATOALKYL-SUBSTITUTED CYCLIC ESTERS

This invention relates to the preparation of nitratoalkyl-substituted cyclic ethers, and in particular to the preparation of nitratoalkyl-substituted oxiranes and oxetanes, from hydroxyalkyl-substituted cyclic ethers.

It is known that nitratoalkyl-substituted cyclic ethers can be prepared directly from their corresponding hydroxyalkyl-substituted precursors.

One such known preparative route is described by L T Eremenko and A M Korolev, (Izvestiya Akademii Nauk SSSR, Seriya Khimicheskaya 5, 1142–1144 (1967)). This single step method consists of reacting an α-epoxy alcohol with a 16:26 w/w mixture of 100% nitric acid and acetic anhydride at a temperature of $-10°$ C. for 20 minutes. However, although a high yield of epoxy alcohol is recoverable from the water-quenched reaction mixture (for example a yield of 81% of glycidyl nitrate is reported from glycidol), this method also has several disadvantages.

One disadvantage of the method of Eremenko and Korolev is that it requires the use of an unstable and potentially dangerous nitrating mixture (nitric acid and acetic anhydride) which is known to generate internally the unstable explosive acetyl nitrate. Such mixtures when containing more than 50% by weight of nitric acid in acetic anhydride are especially dangerous, having been shown by T A Brown & J A C Watt (Chemistry in Britain 3(11), 504 (1967)) to act as detonating explosives. For safety reasons the content of nitric acid in the mixture must therefore be maintained at considerably below 50% by weight. Since the method of Eremenko and Korolev requires a molar excess of nitric acid (a molar excess of about 60% is reported) to ensure the nitration reaction goes to completion, then this excess has to be matched by an even greater quantity by weight of acetic anhydride. This relatively large quantity of acetic anhydride present in the reaction mixture represents a wasted component, since it does not take part in the primary nitration reaction but is nevertheless consumed, mainly by conversion to acetic acid during the course of the reaction and the subsequent quenching of the reaction mixture in aqueous solution. This in turn creates the problems of disposing large quantities of waste acid.

A further disadvantage of the method of Eremenko and Korolev is that even after several washings with aqueous solutions, the epoxy nitrate products are found to be contaminated with appreciable amounts (2.5% w/w reported) of dinitro acetates.

A further known method in the field of the present invention is described in U.S. Pat. No. 3,058,994, in which nitratoalkyl-substituted oxetanes are prepared by the slow addition of a slight molar excess of $N_2O_5$ in organic solvent to a stirred, cooled mixture of an hydroxyalkyl-substituted oxetane. Nitric acid is formed as a byproduct from the exothermic reaction involved. Although this method reportedly produces good yields of nitratoalkyl product, it is not readily adapted to large scale manufacturing processes and leads to the presence of increasing quantities of potentially explosive nitratoalkyl product within the exothermic reaction mixture which slowly build up as the $N_2O_5$ is added. Furthermore, the analogous reaction with more reactive hydroxyalkyl-substituted oxiranes (glycidol, for example) has been shown in published European Patent Application No EP-0223441-A1 to produce rapid rupturing of the oxirane ring and so prevents isolation of a corresponding nitratoalkyl-substituted oxirane product.

It is one object of the present invention to provide a method of nitration which ovecomes at least some of the disadvantages mentioned above and is applicable to the preparation of both nitratoalkyl oxetanes and nitratoalkyl oxiranes. It is a further object of the invention to provide a method whereby the yield and purity of the nitratoalkyl cyclic ether products is improved over those reported in the methods described above.

Accordingly, the present invention provides a process for the preparation of a nitratoalkyl-substituted cyclic ether which comprises the steps of (a) cocurrently mixing streams of an hydroxyalkyl-substituted cyclic ether and $N_2O_5$ to form a reaction mixture as a product stream containing said nitratoalkyl-substituted cyclic ether and nitric acid, and (b) rapidly separating said nitric acid from the reaction mixture.

The $N_2O_5$ is preferably added in an inert solvent, that is, a solvent which does not react with either reactant at the reaction temperatures employed. The solvent is preferably an organic solvent, more preferably a $C_1$–$C_2$ chloroalkane such as carbon tetrachloride, chloroform, methylene chloride, ethylene dichloride and dichloromethane. Dichloromethane is the most preferred solvent. By the use of a solvent, the cocurrent addition of $N_2O_5$ (which would otherwise be present as a gas) is facilitated and the products and reagents of the present reaction are diluted to supress the formation of polymers whose production may be catalysed by the presence of the nitric acid coproduct. Furthermore, the solvent acts a heat sink to prevent the temperature of the exothermic reaction between the $N_2O_5$ and the hydroxyalkyl reagents from rising too high. For these reasons the amount of solvent used is preferably sufficient to maintain the concentration of cyclic ether (product + reagent) in the product stream at less than 2 mols $liter^{-1}$.

The hydroxyalkyl-substituted cyclic ether will generally contain from 2 to 5 carbon atoms in the ether ring and is preferably an oxirane or oxetane. The ether may be substituted with more than one hydroxyalkyl group. The hydroxyalkyl substituent group is preferably a $C_1$–$C_5$ hydroxyalkyl group. Examples of oxiranes which may be used in the present process are glycidol and 3,4-epoxy butanol. Examples of oxetanes which may be used are 3-hydroxymethyl-3-methyloxetane, 3-hydroxymethyl-3-ethyloxetane, 3-hydroxymethyl-3-chloromethyl-oxetane, and 3,3-bishydroxymethyloxetane. The ether is preferably added to the reaction mixture in an inert solvent which is preferably the same as that used as an inert carrier for the $N_2O_5$.

In order to suppress opening of the cyclic ether ring the residence time of nitroalkyl product in the reaction stream before its separation is preferably less than 2 minutes, and, where the cyclic ether is an oxirane which has been found to be the most reactive of the cyclic ethers, the residence time is preferably less than 1 minute, more preferably less than 30 seconds, and is most preferably between 2 and 15 seconds. Side reactions are further suppressed by cooling the product stream to maintain its temperature between $-40°$ C. and $+40°$ C., preferably between $-20°$ C. and $+20°$ C.

The hydroxyalkyl cyclic ether is preferably reacted with molar excess of $N_2O_5$, of preferably in the range 1.01 to 1.5, most preferably 1.05 to 1.2, moles of $N_2O_5$ per mole of hydroxyl groups present in the cyclic ether reagent. This serves to ensure complete and rapid conversion of the hydroxyalkyl substituent groups to nitratoalkyl substitutent groups.

The dinitrogen pentoxide used in the present method may be prepared by any suitable process, but is preferably prepared by the known reaction of dinitrogen tetroxide with ozone.

Step (b) of the present method preferably comprises quenching the reaction mixture in an aqueous solution, into which nitric acid and any remaining $N_2O_5$ are rapidly transferred to leave the nitratoalkyl product in the organic phase. The dilute nitric acid solution thus formed is relatively unreactive towards the nitratoalkyl product remaining in the organic phase. This acidic solution is preferably neutralised with base, preferably inorganic base, before the aqueous and organic phases are separated. This not only helps to remove the final traces of acid from the organic phase, but also produces a salt solution in the aqueous phase which inhibits losses of the water soluble nitratoalkyl product through the aqueous phase when the two phases are separated. The base is preferably present within the aqueous solution used to quench the reaction mixture, although as an alternative it may be added subsequently. Thereafter, the nitratoalkyl product may be recovered from the organic phase.

The main advantage of the invention is that by cocurrently mixing the two principal reagents of the present process, the hydroxyalkyl reagent is rapidly converted to nitratoalkyl and nitric acid coproducts which flow away from fresh hydroxyalkyl reagent fed to the reaction mixture, leading to high product yields and purity. It has been discovered that a nitratoalkyl-substituted cyclic ether is less sensitive to ring-opening attack by nitric acid than its hydroxyalkyl-substituted counterpart. Therefore, the two principal coproducts of the process can coexist for a short period without reacting with one another, providing sufficient time for the reagent to undergo complete reaction before the coproducts are separated. It is another feature of cocurrent mixing that the molar concentration of $N_2O_5$ can be maintained at or above that of the hydroxyalkyl reagent throughout the reaction. This further suppresses any competing reaction between the hydroxyalkyl reagent and the nitric acid coproduct. Another advantage of the process, which is well adapted to the continuous manufacture of the desired nitratoalkyl product, is that it has been found that only very short reaction times are generally required before separating the coproducts, preferably by quenching in basic aqueous solution. This not only obviates the need for large and expensive reaction vessels which would be required for continuous manufacture if long reaction times were found to be necessary, but also means that the present process is inherently safe because only relatively small quantities of nitratoalkyl product will be present in the exothermic reaction stream for any given rate of production.

The present invention will now be described by way of example only with reference to the accompanying drawing in which FIG. 1 is a diagrammatic view of an apparatus for carrying out the present nitration process.

Apparatus

Referring to FIG. 1, two storage vessels 1 and 2 hold, respectively, reservoirs of a hydroxyalkyl-substituted cyclic ether and $N_2O_5$ each dissolved in an inert organic solvent. The vessels 1 and 2 are immersed in a bath 3 through which is continuously fed a liquid coolant. The spaces above the reagents in the vessels 1 and 2 are continuously flushed with dry nitrogen which is vented through outlets 1A and 2A. The outlets 1A and 2A are also used to replenish the reservoirs 1 and 2 respectively with fresh reagent solutions.

The solutions of hydroxyalkyl-substituted cyclic ether and $N_2O_5$ are pumped continuously and simultaneously through a twin-head, PTFE-lined piston pump 4 into a flow reactor 5 through its two inlets. The two solution streams combine and mix within this reactor, aided by a porous filling consisting of glass beads 6 contained between glass wool stoppers 7 and 8. The flow reactor 5 is provided with a jacket 9 through which liquid coolant is continuously pumped in order to cool the exothermic reaction between the $N_2O_5$ and hydroxyalkyl cyclic ether. A thermocouple (not shown) inserted through a PTFE cap 11 into the reactor 5 is used to monitor the temperature of the reaction mixture.

The resultant reaction mixture containing nitratoalkyl cyclic ether and nitric acid flows upwards through a tube 12 to reach a maximum level 13 and thereafter spills over and flows rapidly downwards through a further tube 14 into an open quench tank 15 containing a large excess of inorganic base dissolved in aqueous solution. This basic solution serves to separate the nitric acid and nitratoalkyl coproducts into two separate phases, with the former transferring to the aqueous phase and the latter remaining in the organic phase, and to neutralise the acid so preventing any reaction between the coproducts. The solution is vigorously stirred with a mixer 16 throughout the addition of the reaction mixture to the quench tank 15.

Materials

Glycidol (2,3-epoxypropanol; 2-(hydroxymethyl)oxirane), was supplied by Aldrich Chemical Company. It contained up to approximately 25% homopolymer, and was distilled on Kugelrohr before use. Its boiling point was approximately 140° C. at 20 mm Hg pressure.

$N_2O_5$ (Dinitrogen pentoxide) free from nitric acid and lower oxides of nitrogen was prepared by the oxidation of dinitrogen tetroxide ($N_2O_4$) with ozone. In view of the thermal instability of $N_2O_5$, during its preparation a temperature of less than 30° C. and preferably less than 20° C. was employed throughout. All operations were carried out under anhydrous conditions since $N_2O_5$ is readily hydrolysed to nitric acid. An ozone/oxygen mixture, from a commercially available ozoniser was passed into a glass vessel containing $N_2O_4$. Oxidation occured in the gas phase and the resulting $N_2O_5$ was carried in the oxygen stream and trapped in a series of cold traps kept at −78° C. using a mixed card-ice/acetone coolant. Any unreacted $N_2O_4$ was subsequently reacted by resubliming the initial trapped product in an ozonised oxygen stream. The colourless white crystals of $N_2O_5$ produced could be stored at −78° C. for at least 7 days before use without any noticeable decomposition, and were found to have a melting point well above room temperature.

Dichloromethane (methylene chloride) was distilled before use from $CaH_2$.

3-Hydroxymethyl-3-methyloxetane was supplied by Aldrich Chemical Company, Dorset, UK.

Safety Note

The nitration reactions described below were carried out in an armoured cupboard with fume extraction. Solutions of $N_2O_5$ are corrosive so rubber gloves and a face mask were worn when these solutions were handled.

EXAMPLE 1

Using the apparatus illustrated in FIG. 1, vessels 1 and 2 each of 1 L capacity were charged with, respectively, 63 g glycidol and 101 g $N_2O_5$ each dissolved in 800 ml dichloromethane. A mixed ethylene glycol/water coolant supplied at a temperature of $-10°$ C. was continuously pumped through the bath 3 and jacket 9. The tank 15 (5 liter capacity) was charged with 1.5 L of a 10 wt % sodium bicarbonate solution.

The $N_2O_5$ and glycidol solutions were continuously pumped to the flow reactor 5 each at an average flowrate of 50 ml min$^{-1}$. For equal flows of the two reagent solutions, this equated to a 10% excess of $N_2O_5$ in the flow reactor. The average residence time of the mixture within the flow reactor to the level 13 was approximately 5 seconds. The flow of coolant through the jacket 9 was set to produce a product stream outlet temperature of 16°-18° C.

The process was operated continuously until both vessels 1 and 2 were virtually empty. Thereafter, the mixer 16 was switched off and the organic and aqueous phases allowed to settle out. The organic phase was then separated from the aqueous phase, washed twice with distilled water, and dried over $MgSO_4$. Finally, the dichloromethane solvent was removed on a rotary evaporator.

The yield of organic product (identified as glycidyl nitrate), was found to be greater than 97% based on glycidol. Its hplc purity was 99.6%.

EXAMPLE 2

The process of Example 1 was repeated, using (in vessel 1) 60 g of 3-hydroxymethyl-3-methyloxetane (HMMO) in 800 ml dichloromethane and (in vessel 2) 93 g $N_2O_5$ in 850 ml dichloromethane. The flowrates of the $N_2O_5$ and HMMO solutions to the flow reactor were each set at an average of 35 ml min$^{-1}$. For equal flows of the two reagent solutions, this equated to a 15% excess of $N_2O_5$ in the flow reactor. The coolant flow to the jacket was set to control the exit temperature of the product stream from the reactor at 12°-15° C. The average residence time of the mixture within the flow reactor to the level 13 was approximately 7 seconds.

The process was operated continuously until vessel 1 containing the HMMO solution was empty. Thereafter the product, identified as 3-nitratomethyl-3-methyloxetane, was separated and isolated in the same manner as that described in Example 1. The yield of product was 98.8% based on HMMO. Its hplc purity was 99.8%.

We claim:

1. A process for the preparation of a nitratoalkyl-substituted cyclic ether by the nitration of an hydroxyalkyl-substituted cyclic ether, characterised by the steps of
   (a) cocurrently mixing a first stream of the hydroxyalkyl-substituted cyclic ether with a second stream of $N_2O_5$ to form a reaction mixture as a product stream in which said nitratoalkyl-substituted cyclic ether and nitric acid are formed as co-products, the second stream containing a molar excess of $N_2O_5$ with respect to the hydroxyl groups present in the hydroxyalkyl-substituted cyclic ether in the first stream, and
   (b) rapidly separating said nitric acid from the reaction mixture.

2. Process according to claim 1 wherein the cyclic ether contains from 2 to 5 carbon atoms in the ether ring.

3. Process according to claim 2 wherein the cyclic ether is an oxirane.

4. Process according to claim 2 wherein the cyclic ether is an oxetane.

5. Process according to claim 1 wherein the $N_2O_5$ and, optionally, the hydroxyalkyl-substituted cyclic ether, is dissolved in an inert solvent.

6. Process according to claim 5 wherein the solvent is an organic solvent.

7. Process according to claim 6 wherein the solvent is a $C_1$-$C_2$ chloroalkane.

8. Process according to claim 5 wherein the total amount of solvent present in the product stream is sufficient to maintain the concentration of cyclic ether therein below 2 mol liter$^{-1}$.

9. Process according to claim 1 wherein residence time of the product stream prior to step (b) is less than 2 minutes.

10. Process according to claim 1 wherein the molar ratio of $N_2O_5$ present in the stream of $N_2O_5$ to hydroxyl groups present in the stream of hydroxyalkyl-substituted cyclic ether combined to form the reaction mixture is in the range 1.01:1 to 1.5:1.

11. Process according to claim 1 wherein step (b) comprises quenching the product stream in aqueous solution.

12. Process according to claim 11 wherein said aqueous solution contains a base dissolved therein.

13. Process according to claim 12 wherein the amount of base dissolved in the aqueous solution is in excess of that required to neutralise the nitric acid formed as a byproduct of the reaction of step (a).

14. Process according to claim 1 wherein the product stream is formed continuously.

* * * * *